United States Patent [19]
Davis et al.

[11] 3,987,193
[45] Oct. 19, 1976

[54] PESTICIDAL DIHALOVINYL-SPIROALKANECYCLOPROPANE DERIVATIVES

[75] Inventors: Royston H. Davis, Rainham; Robert J. G. Searle, Sittingbourne, both of England

[73] Assignee: Shell Oil Company, Houston, Tex.

[22] Filed: Aug. 20, 1975

[21] Appl. No.: 606,145

Related U.S. Application Data

[62] Division of Ser. No. 561,573, March 24, 1975, Pat. No. 3,961,070.

[30] Foreign Application Priority Data

Dec. 3, 1974  United Kingdom............... 52224/74

[52] U.S. Cl. .......................... 424/305; 260/468 G; 424/304
[51] Int. Cl.² ..................... A01N 9/24; C07C 69/74
[58] Field of Search ........................ 424/306, 305; 260/468 H, 468 G

[56] References Cited
UNITED STATES PATENTS

| | | | |
|---|---|---|---|
| 3,766,218 | 10/1973 | Ueda et al. .......................... | 424/306 |
| 3,823,177 | 7/1974 | Fanta et al. .......................... | 424/305 |
| 3,927,068 | 12/1975 | Searle et al. .......................... | 424/306 |

*Primary Examiner*—V. D. Turner

[57] ABSTRACT

Compounds of the formula

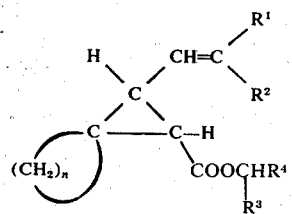

wherein $R^1$ and $R^2$ each is a halogen atom, $R^3$ is hydrogen, alkynyl or cyano; $R^4$ is phenoxyphenyl and $n$ is an integer from 2 to 5, are useful as pesticides.

11 Claims, No Drawings

PESTICIDAL DIHALOVINYL-SPIROALKANECYCLOPROPANE DERIVATIVES

This is a division of application Ser. No. 561,573, filed Mar. 24, 1975, now U.S. Pat. No. 3,961,070.

BACKGROUND OF THE INVENTION

1. Field of the Invention

The present invention relates to novel esters of certain cyclopropane derivatives which exhibit pesticidal properties, especially insecticidal and acaricidal properties. The invention also relates to pesticidal compositions comprising the novel esters and to a method of combating insect or acarid pests.

2. Description of the Prior Art

It is well known that certain substituted cyclopropane carboxylic acid derivatives are an important class of insecticides called "synthetic pyrethroids". These synthetic pyrethroids have been of considerable interest because of their quick knock-down activity, low persistence as toxic residues and their low mammalian toxicity. Literally hundreds of articles and patents have been published with teachings directed to this class of insecticidal compounds.

In our prior U.S. patent application, Ser. No. 510,197, filed Sept. 30, 1974, now U.S. Pat. No. 3,950,535, we disclose certain novel cyclopropane derivatives that conform to the formula

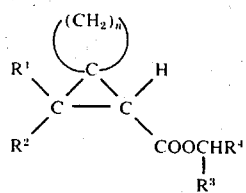

in which $R^1$ and $R^2$ are alkyl, $R^3$ is hydrogen, alkynyl or cyano, $R^4$ is preferably a substituted phenyl group, such as 3-phenoxyphenyl and n is an integer of from 2–5.

Many prior art insecticidal esters have been prepared featuring differences in either the alcohol or acid portion of the ester molecule. U.S. Pat. No. 3,823,177, July 9, 1974 relates to certain spiro-carboxylic acids and their allethrolone esters. U.S. Pat. No. 3,786,052, Jan. 15, 1974 relates to numerous cyclopropane carboxylic acids and esters including allethrolone esters of 2-(isobut-1'-enyl)spiro[2,5]octane-1-carboxylic acid, 2-(isobut-1'-enyl)spiro[2,4]heptane-1-carboxylic acid and 2,2,5-trimethylspiro[2,5]oct-4-ene-1-carboxylic acid. Netherlands publication No. 7307,130, Nov. 27, 1973 relates to esters of dihalovinyldimethylcyclopropane carboxylic acids which esters may be α-substituted on the alcohol moiety by a cyano or ethynyl group. U.S. Pat. No. 3,835,176, Sept. 10, 1974 relates to α-cyanobenzyl cyclopropane carboxylates such as α-cyano-3-phenoxybenzyl 2',2'-dimethyl-3'-vinylcyclopropane carboxylate. U.S. Pat. No. 3,758,504, Sept. 11, 1973 relates to various vinylcyclopropane carboxylates including 3-phenoxybenzyl 2',2'-dimethyl-3'-vinylcyclopropane carboxylate.

SUMMARY OF THE INVENTION

The present inventors have discovered a new class of compounds not previously recognized in the prior art. This new class of compounds is characterized by a cyclopropane carboxylic acid moiety formed of a dihalovinyl substituent on a spiroalkanecyclopropane nucleus. The alcohol moiety is derived from phenoxybenzyl alcohols which may be optionally substituted on the α-carbon atom by a substituent containing a triple bond (—C ≡ ), notably a cyano or alkynyl group. This new class of compounds has readily useful properties as pesticides, particularly against a broad spectrum of insects and acarids. Thus, the new class of compounds of the present invention by reason of their spectrum of activity and their relatively low mammalian toxicity find utility as agricultural pesticides for field application to crops and for certain domestic uses.

DESCRIPTION OF THE PREFERRED EMBODIMENT

Accordingly, the present invention provides dihalovinyl-spiroalkanecyclopropane derivatives having the formula

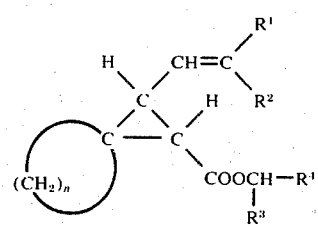

wherein $R^1$ and $R^2$ independently each represents a halogen atom, especially chlorine or bromine; $R^3$ represents a hydrogen atom, alkynyl of 2 to 4 carbon atoms, especially ethynyl, or a cyano group; $R^4$ represents phenyl substituted by phenoxy, especially 3-phenoxyphenyl, and n is an integer of from 2 to 5.

Because of their insecticidal activity level, preferred dihalovinyl-spiroalkanecyclopropane derivatives are those of formula I wherein $R^1$ and $R^2$ each represents a halogen atom, especially chlorine; $R^3$ represents a hydrogen atom, ethynyl or a cyano group; and n is an integer of from 2 or 3.

By reason of their high level of insecticidal activity particularly preferred dihalovinyl-spiroalkanecyclopropane derivatives are those of formula I wherein $R^1$ and $R^2$ each represents a chlorine atom; $R^3$ represents a hydrogen atom or a cyano group, and n is 3. Particular species of this subclass of dihalovinyl-spiroalkanecyclopropane derivatives that are of interest are:

α-cyano-3-phenoxybenzyl-2-(2,2-dichlorovinyl)-3-spirobutane-cyclopropane-1-carboxylate 3-phenoxybenzyl-2-(2,2-dichlorovinyl)-3-spirobutane-cyclopropane-1-carboxylate The cyclopropane derivatives can exist in several isomeric and optically isomeric forms, such as cis-configuration, trans-configuration, dextrorotatory and levorotatory forms of each configuration and mixtures and racemates thereof which are within the scope of the present invention.

The cyclopropane derivatives according to the present invention may be prepared by conventional esterification processes known in the art using reactants of appropriate structure.

The acid reactant to be esterified is a dihalovinyl-spiroalkanecyclopropane carboxylic acid. Such acids are prepared by treating a dihalalkylidenylcycloalkane with ethyl diazoacetate at elevated temperature in the presence of copper-bronze. The resulting ethyl ester is treated with sodium hydroxide and then with acid to yield the free dihalovinyl-spiroalkanecyclopropane carboxylic acid.

As mentioned above the cyclopropane derivatives according to the invention are of interest as pesticides and the invention therefore includes pesticidal compositions comprising a carrier and/or a surface active agent together with a cyclopropane derivative of formula I. Likewise the invention also includes a method of combating insect or acarid pests at a locus which comprises applying to the locus a cyclopropane derivative or composition according to the invention.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing agent or a wetting agent; it may be non-ionic or ionic.

Any of the carrier materials or surface-active agents usually applied in formulating pesticides may be used in the compositions of the invention, and suitable examples of these are to be found, for example, in British Patent Specification No. 1,232,930.

The compositions of the invention may be formulated as wettable powders, dusts, granules, solutions, emulsifiable concentrates, emulsions, suspension concentrates or aerosols. Wettable powders are usually compounded to contain 25, 50 or 75% of toxicant and usually contain, in addition to solid carrier, 3–10%w of a dispersing agent and, where necessary, 0–10%w of stabilizer(s) and/or additives, such as penetrants or stickers.

Dusts are usually formulated as a dust concentrate having a similar composition to that of a wettable powder but without a dispersant, and are diluted in the field with further solid carrier to give a composition usually containing ½–10%w of toxicant. Granules are usually prepared to have a size between 10 and 100 BS mesh (1.676 – 0.152 mm), and may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent and, when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0.5–15%w of dispersing agents, 0.1–10%w of suspending agents such as protective colloids and thixotropic agents agents, 0–10%w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example, other compounds possessing pesticidal, especially insecticidal, acaricidal, herbicidal or fungicidal properties.

EXAMPLES

The invention is further illustrated by the following examples. It should be understood, however, that the examples given are for the purpose of illustration only, and are not to be regarded as limiting the invention in any way.

EXAMPLE I 2-(2,2-Dichlorovinyl)-3-spirobutane-cyclopropane carboxylic acid 1,1-Dichloro-1,3 propylidenylcyclobutane, ethyl diazoacetate and copper-bronze were mixed together in petroleum solvent at 80°–100° C and stirred for 7 hours. The residue was purified by chromatography on silica gel using a 1:1 mixture of hexane and dichloromethane as eluent. A ($\pm$) cis-trans mixture of 2-(2,2-dichlorovinyl)-3-spirobutane-cyclopropane carboxylic acid ethyl ester was obtained (yield 50%) as a solid of molecular weight 249.1.

The above ethyl ester was treated with sodium hydroxide and then with acid. The resulting product was purified by crystallization from methanol-water to obtain the free ($\pm$) cis-trans 2-(2,2-dichlorovinyl)-3-spirobutane-cyclopropane carboxylic acid (yield 75%).

Analysis: Calculated for $C_9 H_{10} O_2 Cl_2$: C, 48.9; H, 4.6; Cl, 32.07%. Found: C, 49.1; H, 4.6; Cl, -%.

EXAMPLE II

α-Cyano-3-phenoxybenzyl-2-(2,2-dichlorovinyl)-3-spirobutane-cyclopropane carboxylate 2-(2,2-Dichlorovinyl)-3-spirobutane-cyclopropane carboxylic acid (0.55g), 3-phenoxy-α-cyano-benzyl-bromide (0.7g) and potassium carbonate (0.2g) were mixed together in acetone (50 ml) and stirred for 24 hours. The mixture was then filtered and the filtrate evaporated. The residue was purified by chromatography on silica gel using a 1:1 mixture of hexane and dichloromethane as eluant. A 1:1 ($\pm$) cis-trans mixture was obtained (yield 70%) as an oil ($n_D^{19} = 1.5735$).
N.M.R. data:
trans-vinylhydrogen: 5.65 ppm (doublet)
cis-vinylhydrogen: 6.2 ppm (doublet)
Analysis: Calculated for $C_{23}H_{19}O_3NCl_2$: C, 64.51; H, 4.5: N, 3.3%. Found: C, 64.7; H, 4.6; N, 3.1%.

EXAMPLE III

3-Phenoxybenzyl-2-(2,2-dichlorovinyl)-3-spirobutanecyclopropane-1-carboxylate 2-(2,2-Dichlorovinyl)-3-spirobutane-cyclopropane carboxylic acid (0.5g), 3-phenoxybenzyl bromide (0.6g) and potassium carbonate (0.2g) were mixed together in acetone (50 ml) and slurried for 24 hours. The mixture was filtered and the filtrate evaporated. The residue obtained was separated into the respective cis- and trans isomer by chromotography on silica gel using a 1:20 mixture of acetone in hexane as eluent. The products were obtained as oils.

Analysis: ($\pm$) Trans-isomer ($n_D^{21} = 1.5707$): yield 45%. Calculated for $C_{22}H_{20}O_3NCl_2$: C, 65.5; H, 5.0; Cl, 17.6%. Found: C, 65.6; H, 5.2; Cl, 17.3%.

(±) Cis-isomer ($n_D^{19}$= 1.5759): yield 20%. Calculated for $C_{22}H_{20}O_3NCl_2$: C, 65.5; H, 5.0; Cl, 17.6%. Found: C, 65.7; H, 4.9; Cl, 18.0%.

EXAMPLE IV

Insecticidal and acaricidal activity

The insecticidal and acaricidal activity of the compounds according to the invention was tested as follows:

I. A 1.0% by weight solution in acetone of the compound to be tested was prepared, and taken up in a micrometer syringe. Two to three-day old adult female house flies (*Musca domestica*) were anaesthetized with carbon dioxide, and 1 μl drop of the test solution was brushed off on the ventral abdomen of each, 20 flies being treated. The treated flies were held for 24 hours in glass jars, each containing a little granulated sugar as food for the flies, and the percentage of dead and moribund individuals was then recorded.

II. The compounds were formulated as solutions or suspensions in water containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under-surface of the leaf with the above formulation. Spraying was effected with a spraying machine delivering 450 liters per hectare, the plants passing under the spray on a moving belt. Ten adult 1–2 week-old mustard beetles (*Phaedon cochleariae*) were placed on the spraying leaf of each turnip plant and ten apterous (6-day-old) vetch aphids (*Megoura viciae*) were placed on the sprayed leaf of each broad bean plant. The plants were then enclosed in glass cylinders fitted at one end with a muslin cap. Mortality counts were made after 24 hours.

III. In tests against glass house spider mites (*Tetranychus urticae*), leaf discs cut from French bean plants were sprayed in the manner described under II. 1 hour after spraying, the discs were inoculated with 10 adult mites. Mortality counts were made 24 hours after inoculation.

IV. The compounds were formulated as solutions or fine suspensions in water containing 20% by weight of acetone and 0.05% by weight of Triton D 100 as wetting agent. The formulations contained 0.6% by weight of the compound to be tested. Pairs of leaves are removed from broad bean plants and placed on filter paper inside plastic petri dishes. Immediately prior to testing ten larvae of the Egyptian cotton leafworm (*Spodoptera littoralis*) are transferred onto the leaves and allowed to settle down. Larvae and leaves are sprayed together using a spraying machine delivering 340 liters/hectare, operated under the conveyor belt principle. After spraying the larvae are covered with a petri dish lid. After 24 hours, the percentage of dead and moribund larvae was recorded.

The results of these tests are shown in Table I, in which A denotes complete kill, B some kill and C no kill of the test species.

Table I

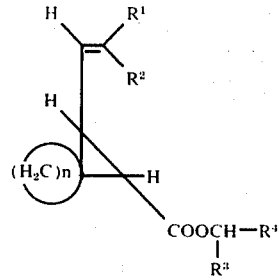

| COMPOUND | | | | | | PESTICIDAL ACTIVITY | | | | |
|---|---|---|---|---|---|---|---|---|---|---|
| $R^1$ | $R^2$ | $R^3$ | $R^4$ | n | cis/trans | M. domestica | P. cochlearias | S. littoralis | M. viciae | T. urticae |
| Cl | Cl | CN | 3-phenoxyphenyl | 3 | c/t | A | A | A | A | A |
| Cl | Cl | H | 3-phenoxyphenyl | 3 | t | A | A | A | A | C |
| Cl | Cl | H | 3-phenoxyphenyl | 3 | c | A | A | A | A | A |

What is claimed is:

1. A dihalovinyl-spiroalkanecyclopropane derivative of the formula

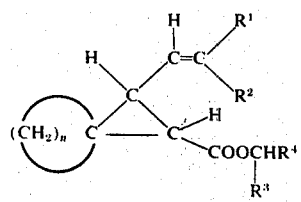

wherein
$R^1$ and $R^2$ independently each represents a halogen atom;
$R^3$ represents a hydrogen atom, or alkynyl of 2 to 4 carbon atoms;
$R^4$ represents phenyl substituted by phenoxy and n is an integer of from 2 to 5.

2. A dihalovinyl-spiroalkanecyclopropane derivative as claimed in claim 1, wherein $R^1$ and $R^2$ each represents a halogen atom; $R^3$ represents a hydrogen atom or ethynyl and n is an integer of from 2 to 3.

3. A dihalovinyl-spiroalkanecyclopropane derivative as claimed in claim 2 wherein $R^1$ and $R^2$ each represents a chlorine atom.

4. A dihalovinyl-spiroalkanecyclopropane derivative as claimed in claim 2 wherein $R^1$ and $R^2$ each represents a chlorine atom; $R^3$ represents a hydrogen atom and *n* is 3.

5. A dihalovinyl-spiroalkanecyclopropane derivative as claimed in claim 4, wherein $R^4$ is 3-phenoxyphenyl.

6. A method of combating insect or arachnid pests at a locus which comprises applying to the locus a pesticidally active amount of a dihalovinyl-spiroalkanecyclopropane derivative of the formula

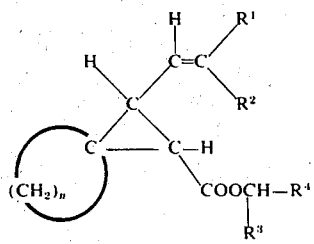

wherein
R$^1$ and R$^2$ independently each represents a halogen atom;
R$^3$ represents a hydrogen atom or alkynyl of 2 to 4 carbon atoms;
R$^4$ represents phenyl substituted by phenoxy and $n$ is an integer of from 2 to 5.

7. A method as claimed in claim 6 wherein R$^1$ and R$^2$ each represents a halogen atom; R$^3$ represents a hydrogen atom or ethynyl; and $n$ is an integer of 2 to 3.

8. A method as claimed in claim 7 wherein R$^1$ and R$^2$ each represents a chlorine atom.

9. A method as claimed in claim 7 wherein R$^1$ and R$^2$ each represents a chlorine atom; R$^3$ represents a hydrogen atom; and n is 3.

10. A method as claimed in claim 9 wherein R$^4$ is 3-phenoxyphenyl.

11. An insecticidal or acaricidal composition comprising at least one carrier or surface-active agent, together with, as active ingredient an insecticidally or acaricidally effective amount of a dihalovinyl-spiroalkanecyclopropane derivative as described in claim 6.

* * * * *